US009355220B2

(12) United States Patent
Paydar et al.

(10) Patent No.: US 9,355,220 B2
(45) Date of Patent: May 31, 2016

(54) MEDICATION DISPENSING CABINET SYSTEMS AND METHODS

(75) Inventors: Akbar Paydar, Mountain View, CA (US); Stanley Kim, Mountain View, CA (US); Chris Richardson, Mountain View, CA (US); John Foot, Mountain View, CA (US); Mahmoud Amini, Mountain View, CA (US); Stuart Morita, Mountain View, CA (US); Jennifer Cartright, Mountain View, CA (US); Kyung-Hee Kang, Mountain View, CA (US); Jeff Blank, Mountain View, CA (US); Scott Gregg, Mountain View, CA (US); Andrew Chai, Mountain View, CA (US)

(73) Assignee: Omnicell, Inc., Mountain View, CA (US)

( * ) Notice: Subject to any disclaimer, the term of this patent is extended or adjusted under 35 U.S.C. 154(b) by 0 days.

(21) Appl. No.: 13/461,578

(22) Filed: May 1, 2012

(65) Prior Publication Data

US 2013/0006415 A1 Jan. 3, 2013

Related U.S. Application Data

(60) Provisional application No. 61/481,368, filed on May 2, 2011, provisional application No. 61/566,931, filed on Dec. 5, 2011.

(51) Int. Cl.
*G06F 17/00* (2006.01)
*G06F 19/00* (2011.01)
(Continued)

(52) U.S. Cl.
CPC ........ *G06F 19/3462* (2013.01); *G07F 17/0092* (2013.01); *G07G 1/009* (2013.01); *G07G 1/0018* (2013.01)

(58) Field of Classification Search
CPC .................................................... G07G 1/0018
USPC .................................................. 700/235, 237
See application file for complete search history.

(56) References Cited

U.S. PATENT DOCUMENTS 4,654,799 A * 3/1987 Ogaki et al. .................. 700/234
4,672,554 A * 6/1987 Ogaki ........................... 700/234

(Continued)

FOREIGN PATENT DOCUMENTS

CN 1541898 A 11/2004
CN 101010115 A 8/2007

(Continued)

OTHER PUBLICATIONS

Author Unknown, "Intel Active Management Technology," Wikipedia, retrieved from http://en.wikipedia.org/wiki/Intel_Active_Management_Technology on Apr. 29, 2011, 11 pages.

(Continued)

*Primary Examiner* — Michael K Collins
(74) *Attorney, Agent, or Firm* — Kilpatrick Townsend & Stockton LLP

(57) ABSTRACT

A medication dispensing cabinet provides controlled access to medications and supplies stored in it. The cabinet may include at least one lockable storage compartment, and a controller that controls access to the at least one lockable storage compartment. The cabinet may include multiple printers integrated into the cabinet. The cabinet may include a camera operably coupled to the controller. The cabinet may include a set of cabinet electronics, and a power distribution and communications circuit board. The cabinet may include a radio frequency identification (RFID) reader, wherein the controller conditions access to the at least one lockable storage compartment on receipt of information from the RFID reader. Data may be stored in the controller according to an implementation of RAID technology. The controller may include multiple electronic communications network interfaces, and may include an out of band network communication channel. A dispensing cabinet may facilitate printing of labels for medications.

4 Claims, 19 Drawing Sheets

(51) Int. Cl.
*G07F 17/00* (2006.01)
*G07G 1/00* (2006.01)

(56) References Cited

U.S. PATENT DOCUMENTS

| | | | |
|---|---|---|---|
| 5,190,185 A | 3/1993 | Blechl | |
| 5,349,534 A | 9/1994 | Rousseff et al. | |
| 5,377,864 A | 1/1995 | Blechl et al. | |
| 5,452,221 A * | 9/1995 | Tumidei | 700/235 |
| 5,745,366 A | 4/1998 | Higham et al. | |
| 5,805,455 A | 9/1998 | Lipps | |
| 5,805,456 A | 9/1998 | Higham et al. | |
| 5,905,653 A | 5/1999 | Higham et al. | |
| 5,927,540 A | 7/1999 | Godlewski | |
| 6,011,999 A | 1/2000 | Holmes | |
| 6,039,467 A | 3/2000 | Holmes | |
| 6,151,536 A | 11/2000 | Arnold et al. | |
| 6,170,929 B1 | 1/2001 | Wilson et al. | |
| 6,272,394 B1 | 8/2001 | Lipps | |
| 6,370,841 B1 * | 4/2002 | Chudy et al. | 53/411 |
| 6,385,505 B1 | 5/2002 | Lipps | |
| 6,471,089 B2 * | 10/2002 | Liff et al. | 221/13 |
| 6,609,047 B1 | 8/2003 | Lipps | |
| 6,640,159 B2 | 10/2003 | Holmes et al. | |
| 6,760,643 B2 | 7/2004 | Lipps | |
| 6,814,255 B2 * | 11/2004 | Liff et al. | 221/13 |
| 6,975,922 B2 | 12/2005 | Duncan et al. | |
| 7,348,884 B2 | 3/2008 | Higham | |
| 7,349,858 B1 * | 3/2008 | McGrady et al. | 705/3 |
| 7,438,222 B2 | 10/2008 | Green et al. | |
| 7,469,820 B2 * | 12/2008 | Rosenblum | 235/375 |
| 7,471,993 B2 * | 12/2008 | Rosenblum | 700/237 |
| 7,571,024 B2 | 8/2009 | Duncan et al. | |
| 7,675,421 B2 | 3/2010 | Higham | |
| 7,685,026 B1 | 3/2010 | McGrady et al. | |
| 7,835,819 B2 | 11/2010 | Duncan et al. | |
| 8,027,749 B2 * | 9/2011 | Vahlberg | G06Q 10/087 700/236 |
| 8,078,317 B2 * | 12/2011 | Allinson et al. | 700/237 |
| 8,342,400 B1 * | 1/2013 | Reese | 235/385 |
| 8,746,908 B2 * | 6/2014 | Michael | F21V 33/0012 362/125 |
| 2002/0032582 A1 * | 3/2002 | Feeney et al. | 705/2 |
| 2003/0055531 A1 * | 3/2003 | Liff et al. | 700/235 |
| 2003/0074218 A1 * | 4/2003 | Liff et al. | 705/1 |
| 2007/0251990 A1 * | 11/2007 | LeNorman | G07F 17/20 235/375 |
| 2007/0252000 A1 * | 11/2007 | LeNorman | G07F 17/20 235/380 |
| 2008/0262649 A1 * | 10/2008 | Allinson et al. | 700/235 |
| 2008/0319579 A1 | 12/2008 | Vahlberg et al. | |
| 2009/0048712 A1 | 2/2009 | Rosenblum | |
| 2010/0017296 A1 | 1/2010 | Spignesi, Jr. et al. | |
| 2010/0042437 A1 | 2/2010 | Levy et al. | |
| 2010/0198401 A1 | 8/2010 | Waugh et al. | |
| 2012/0004770 A1 * | 1/2012 | Ooyen et al. | 700/235 |
| 2012/0253509 A1 * | 10/2012 | Garda et al. | 700/235 |
| 2013/0006415 A1 * | 1/2013 | Paydar | G06F 19/3462 700/235 |
| 2014/0222194 A1 * | 8/2014 | Paradissis et al. | 700/237 |

FOREIGN PATENT DOCUMENTS

| | | |
|---|---|---|
| CN | 101488253 A | 7/2009 |
| JP | 2005-038265 A | 2/2005 |

OTHER PUBLICATIONS

International Search Report and Written Opinion of PCT/US2012/036126 mailed on Jul. 10, 2012, 9 pages.
Extended European Search Report for European Patent Application No. 12779388.3 mailed on Oct. 27, 2015, 11 pages.
Office Action for Chinese Patent Application No. 201280033147.X mailed on Dec. 11, 2015, 14 pages.
Office Action mailed on Jan. 19, 2016 for Japanese Patent Application No. 2014-509387, all pages.

* cited by examiner

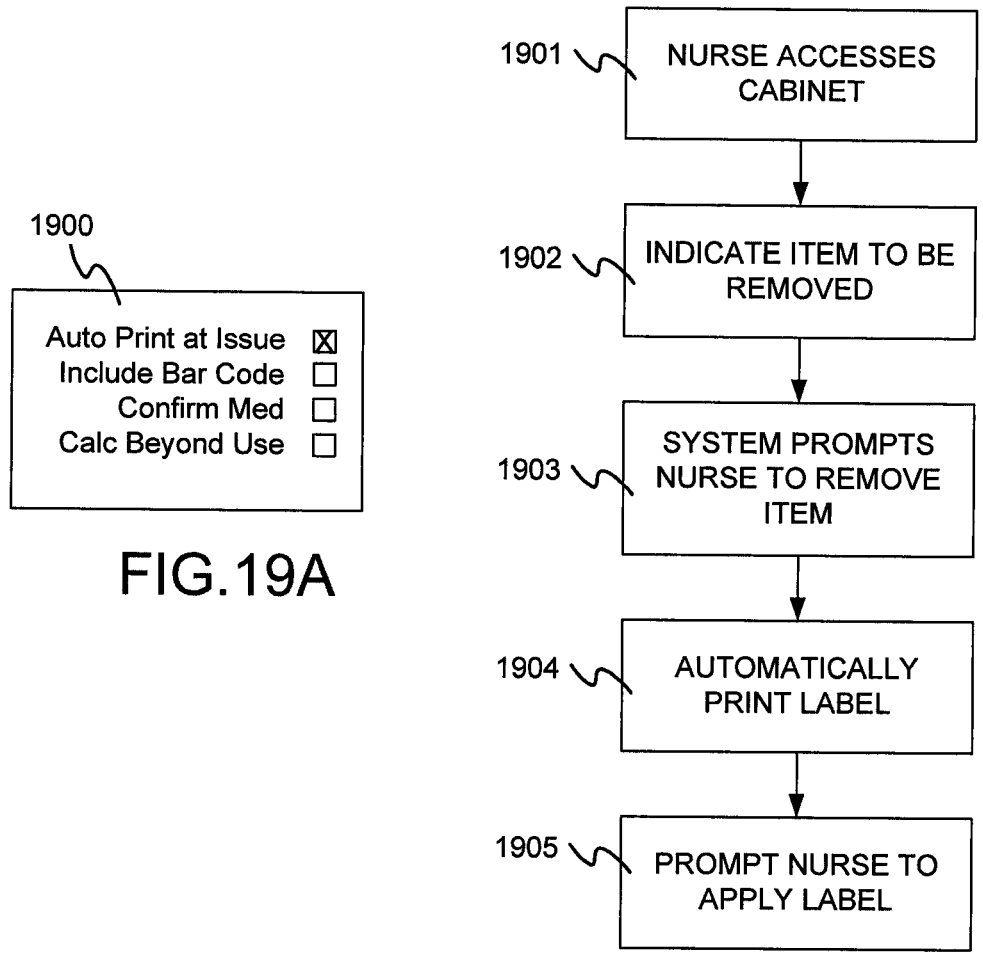
FIG.19A
FIG.19B
FIG.19C

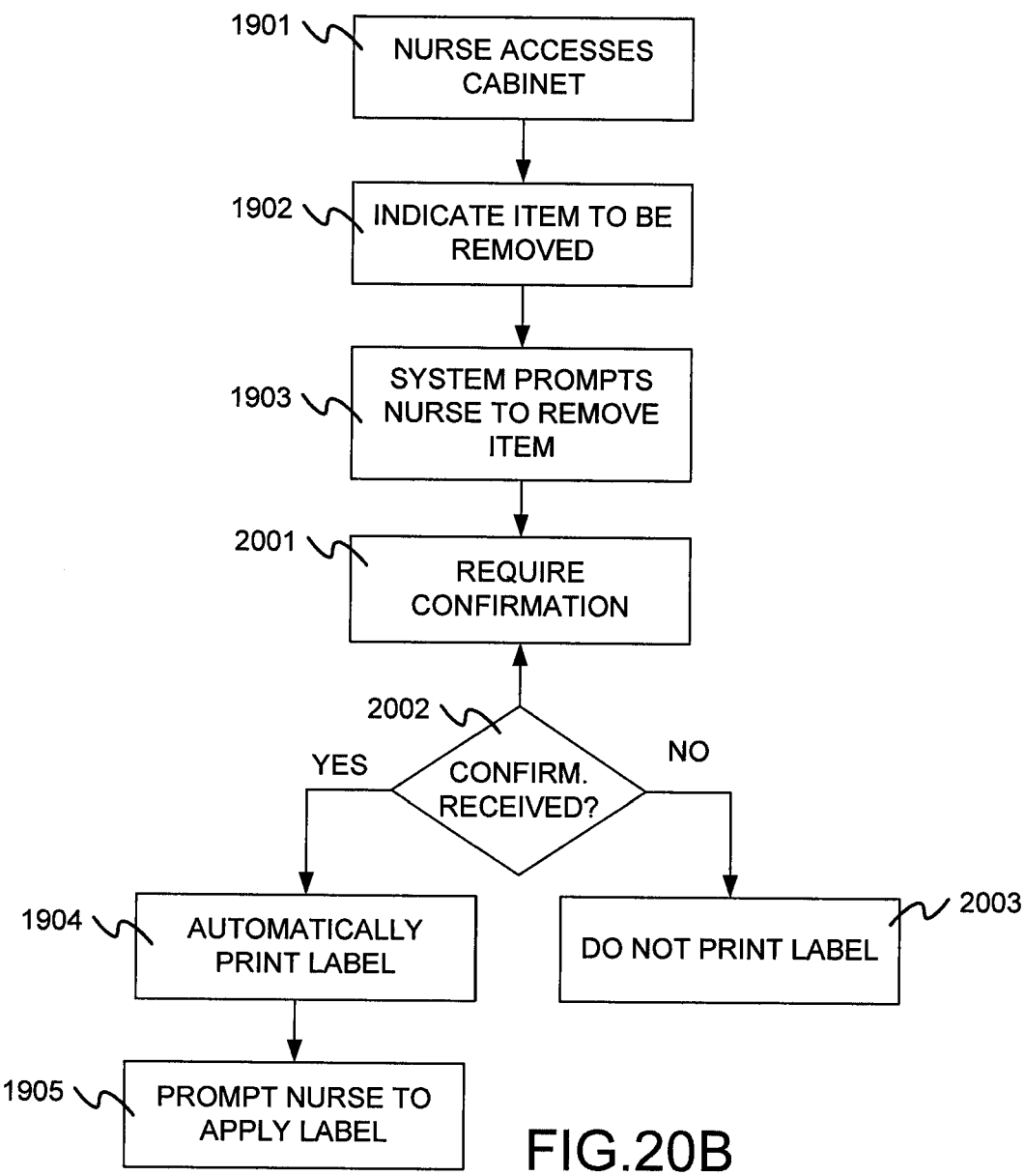

MEDICATION DISPENSING CABINET SYSTEMS AND METHODS

This application claims priority to provisional U.S. Patent Application 61/481,368, filed May 2, 2011 and titled "Medication Dispensing Cabinet Systems and Methods", and to provisional U.S. Patent Application No. 61/566,931, filed Dec. 5, 2011 and titled "Medication Dispensing Cabinet Systems and Methods", the entire disclosures of which are hereby incorporated by reference herein.

BACKGROUND OF THE INVENTION

In a hospital or other patient care setting, a large number of medications and other medical supplies may be used. Different patients typically require different medications, and different medications may be subject to different legal standards for access and control. It is highly desirable that medications and supplies be tracked and access to them be controlled, to avoid medication errors, to avoid illicit access, and to facilitate inventory control and accounting functions.

BRIEF SUMMARY OF THE INVENTION

According to one aspect, a medication dispensing cabinet includes at least one lockable storage compartment, a controller that controls access to the at least one lockable storage compartment, and two printers coupled to the controller and integrated into the medication dispensing cabinet. The printers may include a receipt printer and a label printer. The two printers may mount to a common bezel. In some embodiments, at least one of the printers comprises a printing stock holder for holding a roll of printing stock, and the printing stock holder includes a curved surface shaped to approximately conform to the roll of printing stock, the curved surface including a raised feature formed to be smooth, so as to allow the stock to slide freely as it is dispensed.

According to another aspect, a medication dispensing cabinet includes at least one lockable storage compartment, a controller that controls access to the at least one lockable storage compartment, and a camera operably coupled to the controller. In some embodiments, the camera is positioned to photograph a user of the medication dispensing cabinet. A photograph taken using the camera of a user of the medication dispensing cabinet may be associated with a usage log.

According to another aspect, a medication dispensing cabinet includes at least one lockable storage compartment, a controller that controls access to the at least one lockable storage compartment, a set of cabinet electronics, and a power distribution and communications circuit board. The power distribution and communications circuit board further includes circuitry that provides a first set of required voltage supplies to the controller and provides a second set of required voltage supplies to the cabinet electronics, and the power distribution and communications circuit board routes communication signals between the controller and the cabinet electronics. The circuitry may derive the two sets of required voltage supplies from a single source voltage.

According to another aspect, a medication dispensing cabinet includes at least one lockable storage compartment, a controller that controls access to the at least one lockable storage compartment, and a radio frequency identification (RFID) reader. The controller conditions access to the at least one lockable storage compartment on receipt of information from the RFID reader. In some embodiments, the controller conditions access to the at least one lockable storage compartment on receipt from the RFID reader of information comprising any one or any combination of an identification of a user of the medication dispensing cabinet, a password, and a security code. In some embodiments, the medication dispensing cabinet further includes a biometric sensor. The controller may condition access to the at least one lockable storage compartment on receipt of information from the biometric sensor. In some embodiments, the medication dispensing cabinet further includes a smart card reader. The controller may condition access to the at least one lockable storage compartment on receipt of information from the smart card reader.

According to another aspect, a medication dispensing cabinet includes at least one lockable storage compartment, and a controller that controls access to the at least one lockable storage compartment, the controller comprising data storage media. Data is stored redundantly on the data storage media, according to an implementation of RAID technology.

According to another aspect, a medication dispensing cabinet includes at least one lockable storage compartment, and a controller that controls access to the at least one lockable storage compartment. The controller includes redundant wired electronic communications network interfaces.

According to another aspect, a medication dispensing cabinet includes at least one lockable storage compartment, and a controller that controls access to the at least one lockable storage compartment. The controller includes an out of band network communication channel that is independent of the state of an operating system in the controller.

According to another aspect, a dispensing cabinet includes at least one lockable storage compartment, a controller that controls access to the at least one lockable storage compartment, and a label printer coupled to the controller. The controller is configured such that a label is printed automatically when an item is dispensed from the dispensing cabinet. In some embodiments, confirmation of the identity of the dispensed item is required before a label is printed. In some embodiments, the controller is configurable to include a barcode on the printed label identifying the dispensed item, or to exclude the barcode. In some embodiments, the controller is configurable to include a beyond use date for the dispensed item on the printed label, or to exclude the beyond use date. In some embodiments, a user of the dispensing cabinet can complete issuance of an item from the dispensing cabinet whether or not a label is successfully printed.

According to another aspect, a method of operating a dispensing cabinet includes receiving from a user of the cabinet an indication of a dispensed item, printing a label identifying the item, and prompting the user to affix the label to the dispensed item. The label may be printed automatically upon dispensing of the item. In some embodiments, the method further includes receiving from the user an indication that the label is to be printed. The method may further include requiring confirmation of the identity of the dispensed item. The method may further include printing a barcode on the label, the barcode identifying the dispensed item. In some embodiments, the method further includes printing beyond use date on the label. In some embodiments, the method further includes receiving an indication of a second dispensed item, requiring confirmation of the identity of the second dispensed item, and recognizing that the confirmation is not received, wherein, as a result of the failure to receive the confirmation, no label is printed for the second dispensed item.

BRIEF DESCRIPTION OF THE DRAWINGS

FIG. 19A illustrates an example configuration menu.

FIG. 19B illustrates a workflow for automatic label printing, in accordance with an embodiment.

FIG. 19C illustrates an example printed label.

FIG. 20A illustrates an example configuration menu.

FIG. 20B illustrates a workflow according to an embodiment wherein confirmation of a medication identity is required for label printing.

DETAILED DESCRIPTION OF THE INVENTION

Figure 1:
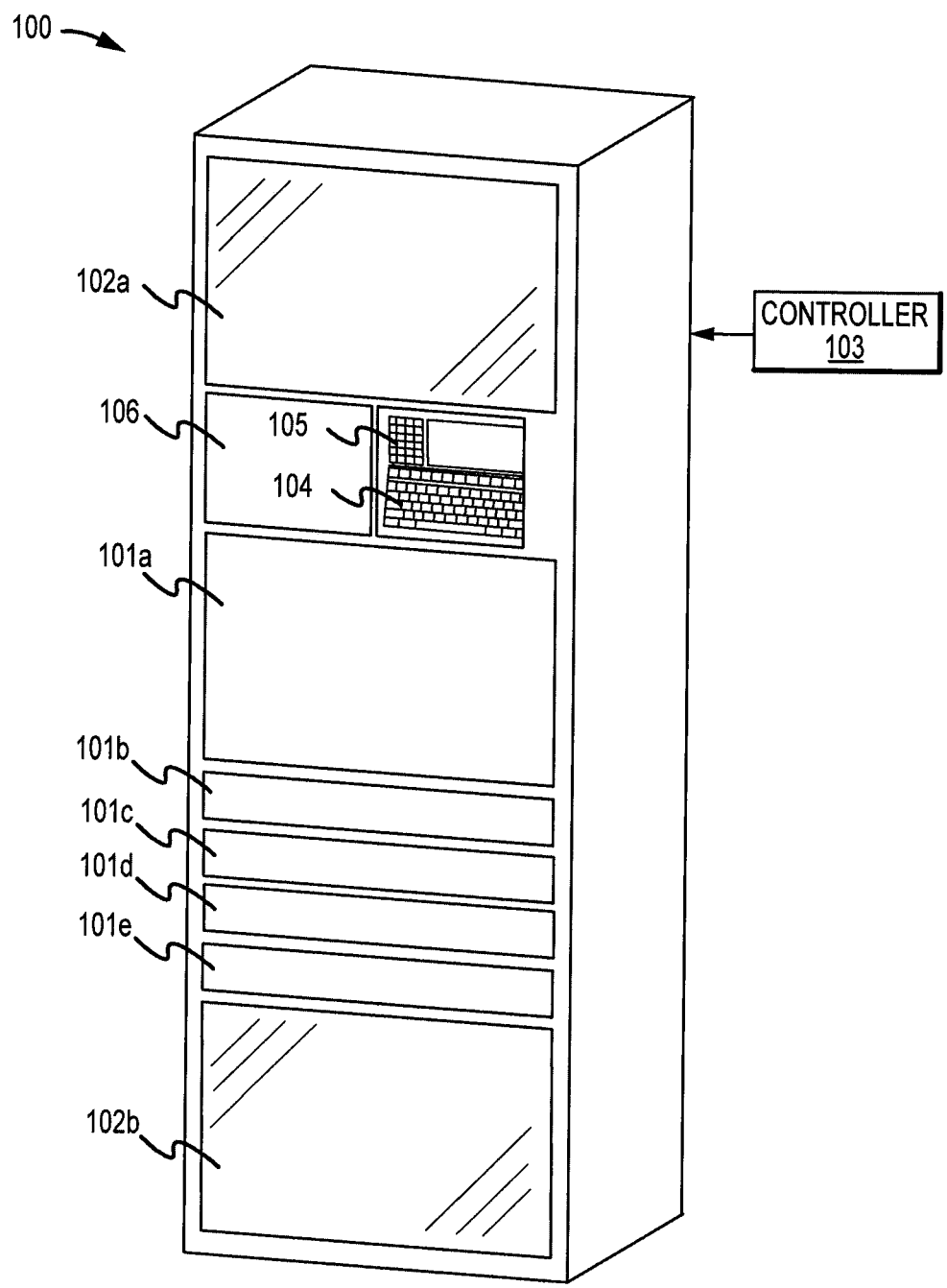
FIG. 1 illustrates a medication dispensing cabinet, in accordance with embodiments.

FIG. 1 illustrates a medication dispensing cabinet 100, in accordance with embodiments. Cabinet 100 includes a plurality of compartments, including drawers 101a-101e, and compartments accessible through doors 102a and 102b. Medication dispensing cabinet 100 also includes a controller 103, and one or more data entry devices such as keyboard 104 and keypad 105. A display 106 enables communication of information to a user of medicine dispensing cabinet 100. In some embodiments, a medication dispensing cabinet may include other devices as discussed in more detail below.

Controller 103 may include a computer, which further includes a processor, memory, input/output interfaces, and other components. Controller 103 may communicate remotely with other computerized systems, such as medical records systems, inventory and accounting systems, and the like.

The various storage compartments such as drawers 101a-101e may be under the control of controller 103. For example, each of drawers 101a-101e may include an electronically-controllable locking mechanism, and may only be openable under the control of controller 103.

In addition, controller 103 may store information about what supplies are stored in which compartments of medication storage cabinet 100. In one typical basic usage scenario, a health care worker may enter, using keyboard 104 or another input device, an identification of a patient who is under the care of the health care worker, and who will need medication during the worker's current rounds. Controller 103 may access the patient's medical file and determine what medications have been prescribed for that patient. Controller 103 may then open only the drawer or drawers containing the prescribed medications for the patient. A particular compartment within the correct drawer may be highlighted, for example with a lighted indicator, to draw the health care worker to the correct medication. The health care worker can then remove the patient's prescribed medication. The level of control exercised by controller 103 may help in preventing medication and dosing errors, by reducing the likelihood that a health care worker will remove an incorrect medication from medication dispensing cabinet 100. In addition, controller 103 may document and record which medication was dispensed, and may forward that information to inventory and accounting systems.

Many other features and functions are possible as well. For example, the health care worker may enter his or her identification as well, and controller 103 may provide access only to those medications and supplies for which the worker is authorized to access.

While medication dispensing cabinet 100 is shown as a stationary device, the invention is not so limited. Cabinets according to other embodiments may be portable, for example to facilitate transporting medications and supplies from a central supply store to a particular ward or department of a facility. It will be recognized that the particular arrangement of drawers, doors, or other features of a cabinet according to embodiments of the invention may be varied. For example, some cabinets or dispensing carts embodying the invention may use only drawers, only doors, or utilize some other access method. Compartments within drawers may also be individually lockable and controllable. Additional types of dispensing units are described in the following commonly owned U.S. Patents and patent applications, the contents of which are hereby incorporated by reference: U.S. Pat. No. 6,272,394, issued on Aug. 7, 2001 to Lipps, U.S. Pat. No. 6,385,505, issued on May 7, 2002 to Lipps, U.S. Pat. No. 6,760,643, issued on Jul. 6, 2004 to Lipps, U.S. Pat. No. 5,805,455, issued on Sep. 8, 1998 to Lipps, U.S. Pat. No. 6,609,047, issued on Aug. 19, 2003 to Lipps, U.S. Pat. No. 5,805,456, issued on Sep. 8, 1998 to Higham et al., U.S. Pat. No. 5,745,366, issued on Apr. 28, 1998 to Higham et al., an U.S. Pat. No. 5,905,653, issued on May 18, 1999 to Higham et al., U.S. Pat. No. 5,927,540, issued on Jul. 27, 1999 to Godlewski, U.S. Pat. No. 6,039,467, issued on Mar. 21, 2000 to Holmes, U.S. Pat. No. 6,640,159, issued on Oct. 28, 2003 to Holmes et al., U.S. Pat. No. 6,151,536, issued on Nov. 21, 2000 to Arnold et al., U.S. Pat. No. 5,377,864, issued on Jan. 3, 1995 to Blechl et al., U.S. Pat. No. 5,190,185, issued on Mar. 2, 1993 to Blechl, U.S. Pat. No. 6,975,922, issued on Dec. 13, 2005 to Duncan et al., U.S. Pat. No. 7,571,024, issued on Aug. 4, 2009 to Duncan et al., U.S. Pat. No. 7,835,819, issued on Nov. 16, 2010 to Duncan et al., U.S. Pat. No. 6,011,999, issued on Jan. 4, 2000 to Holmes, U.S. Pat. No. 7,348,884, issued on Mar. 25, 2008 to Higham, U.S. Pat. No. 7,675,421, issued on Mar. 9, 2010 to Higham, U.S. Pat. No. 6,170,929, issued on Jan. 9, 2001 to Wilson et al., U.S. Patent Application Publication No. 2008/0319579 of Vahlberg et al., published on Dec. 25, 2008, and U.S. Patent Application Publication No. 2010/0042437 of Levy et al., published on Feb. 18, 2010.

A medication dispensing cabinet such as cabinet 100 embodying aspects of the invention may enjoy improved convenience and reliability as compared with prior art cabinets.

In one aspect, a medication dispensing cabinet may provide multiple integrated printers. The different printers may provide different functions that require different media or other characteristics. For example, it may be desirable to provide a printed receipt each time a health care worker removes medication or supplies from cabinet 100. Such a receipt may be placed in a patient's file, or attached to a treatment order. It may also be desirable in some applications to print an adhesive label that describes a particular medication or instructions for use of a particular medication. Such a label may be adhered to a syringe, bottle, or other container into which the medication is transferred. As such, a label printer requires a different kind of media than the receipt printer.

Figure 2:
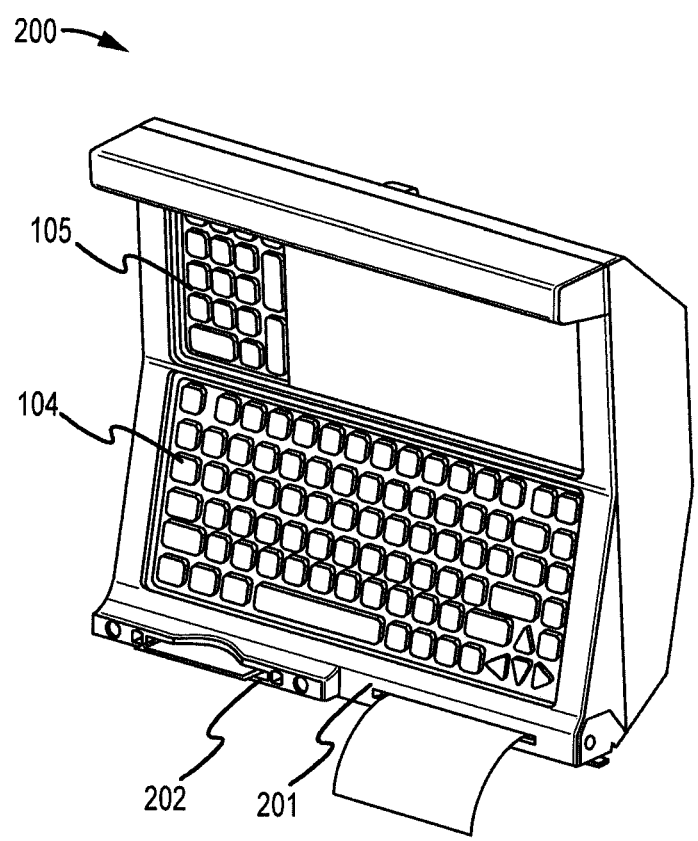
FIG. 2 illustrates a module that provides one example arrangement for integration of two printers into a medication dispensing cabinet such as the medication dispensing cabinet of FIG. 1.

FIG. 2 illustrates a module 200 that provides one example arrangement for integration of two printers into a medication dispensing cabinet such as medication dispensing cabinet 100. Module 200 includes keyboard 104 and keypad 105, and also includes an integrated receipt printer 201 and an integrated label printer 202. Preferably, both printers are modular, and may be field or factory installable. The printers may be independently addressable by controller 103 through universal serial bus (USB) connections or other kinds of interfaces.

In some embodiments, receipt printer 201 may be a thermal printer that prints on relatively light weight print stock. Other kinds of printers could be used as well, for example an inkjet printer. Label printer 202 may be a thermal or inkjet printer, or another kind of printer, that prints on label stock. Once a label is printed, it may be removed from a backing to expose an adhesive, which may then be used to adhere the label to a container.

Figure 3:
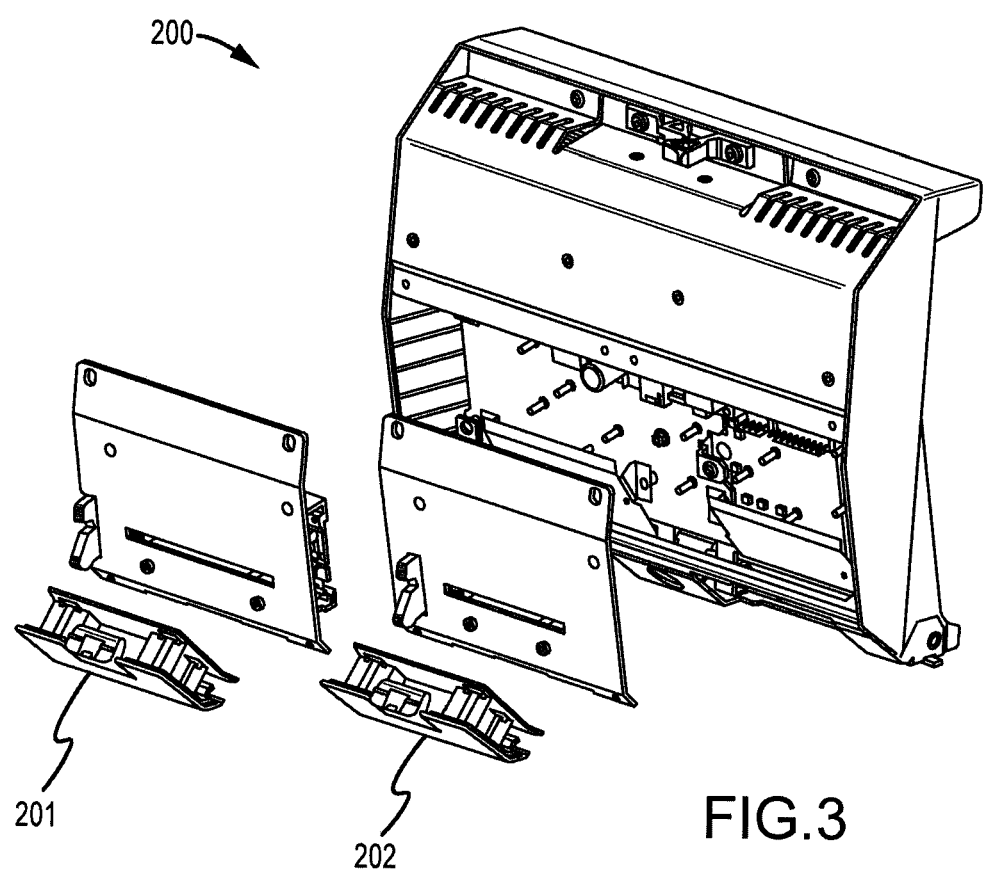
FIG. 3 illustrates a rear view of the module of FIG. 2.

FIG. 3 illustrates a rear view of module 200, showing the mounting of modular receipt printer 201 and label printer 202 into module 200.

Figure 4:
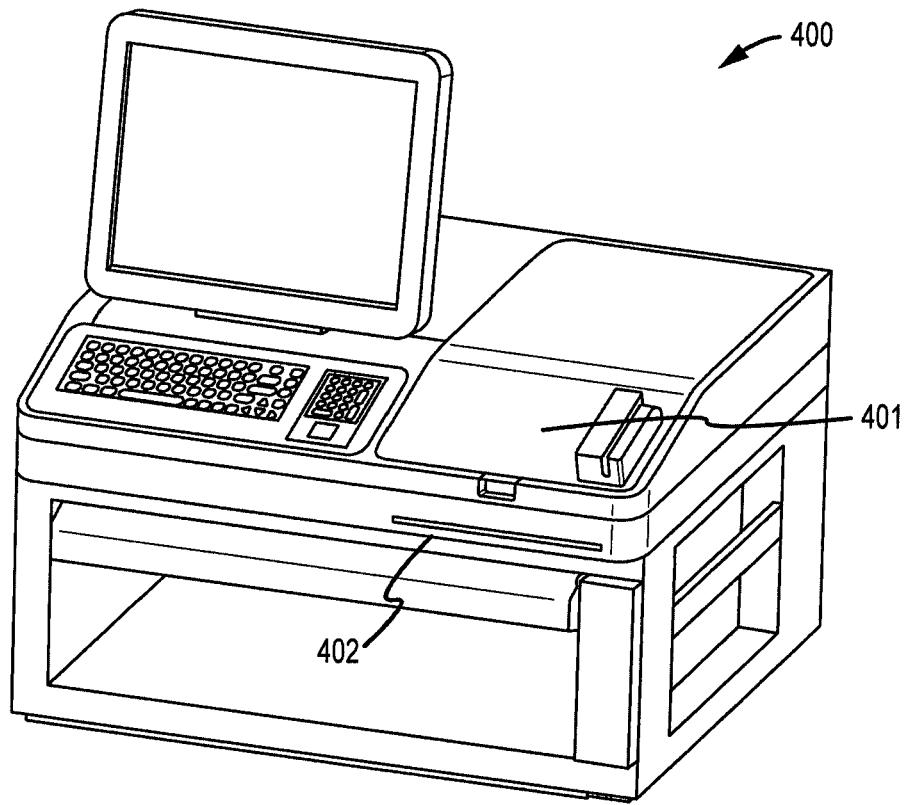
FIG. 4 illustrates a table-top medication dispensing cabinet, in accordance with embodiments.

FIG. 4 illustrates a table-top medication dispensing cabinet 400, which also includes integrated dual printers. The dual printers are housed under a printer door 401, and may share a common opening 402 through which to deliver printed items. Door 401 may be magnetically closed.

Figure 5:
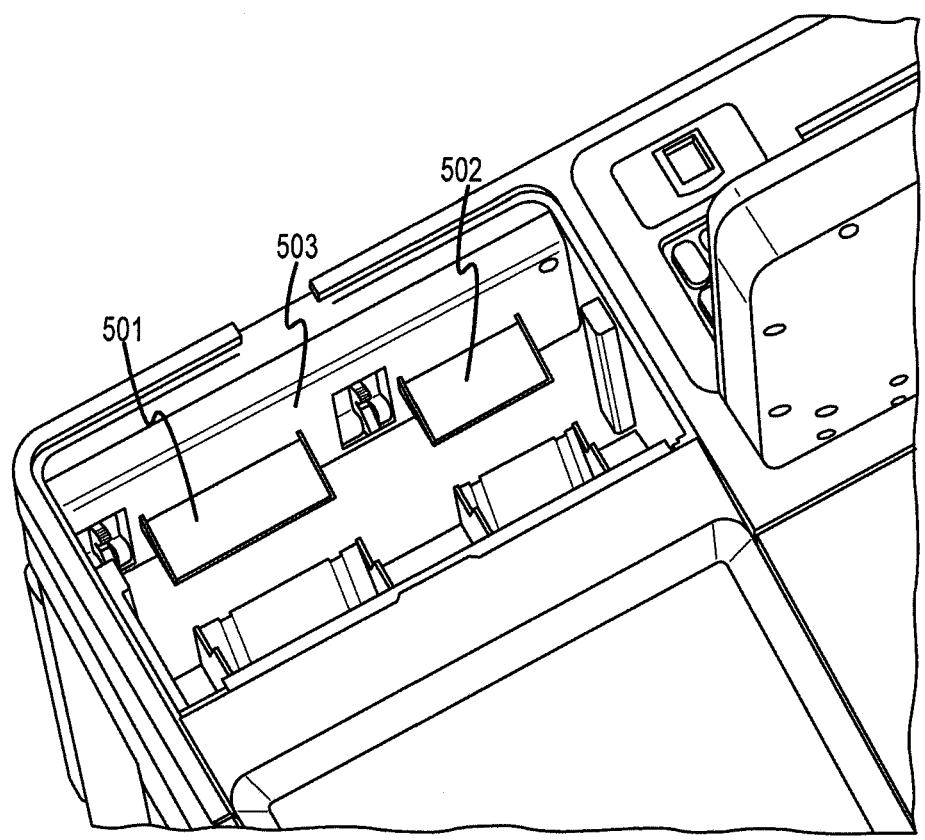
FIG. 5 illustrates an interior view of the medication dispensing cabinet of FIG. 4.
Figure 6:
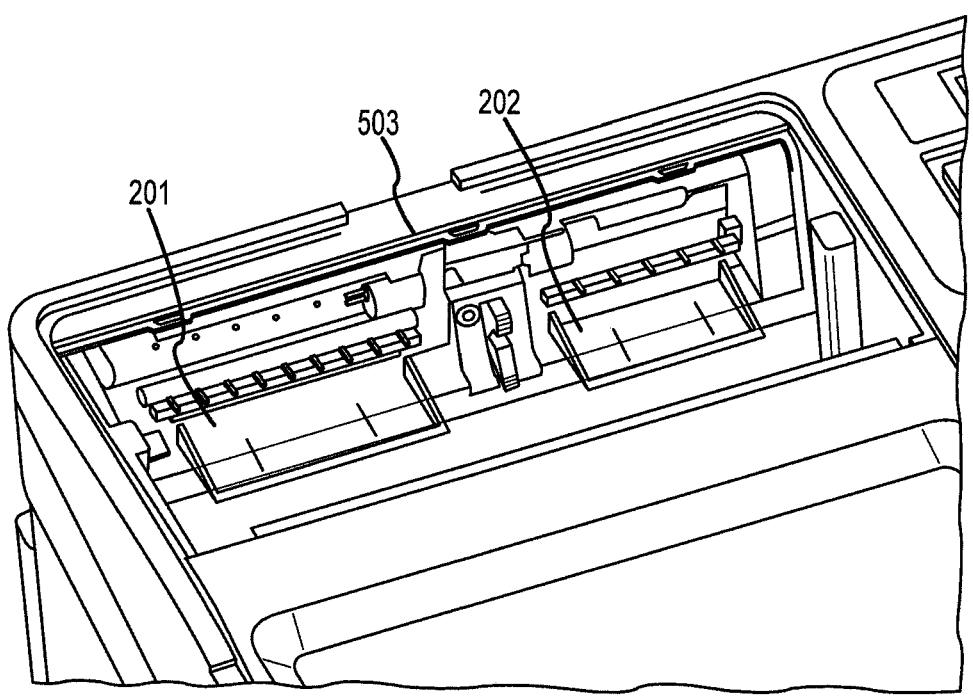
FIG. 6 illustrates the two printers mounted to bezel, in accordance with embodiments.

FIG. 5 illustrates an interior view of medication dispensing cabinet 400, showing receipt printer paper guide 501 and label printer paper guide 502 molded into the rear portion of a common bezel 503. Paper guides 501 and 502 may serve as guides to straighten and align their respective paper rolls with the printer, and may assist a user in manually loading paper by sliding the paper along the guides. FIG. 6 illustrates the two printers mounted to bezel 503.

Figure 7:
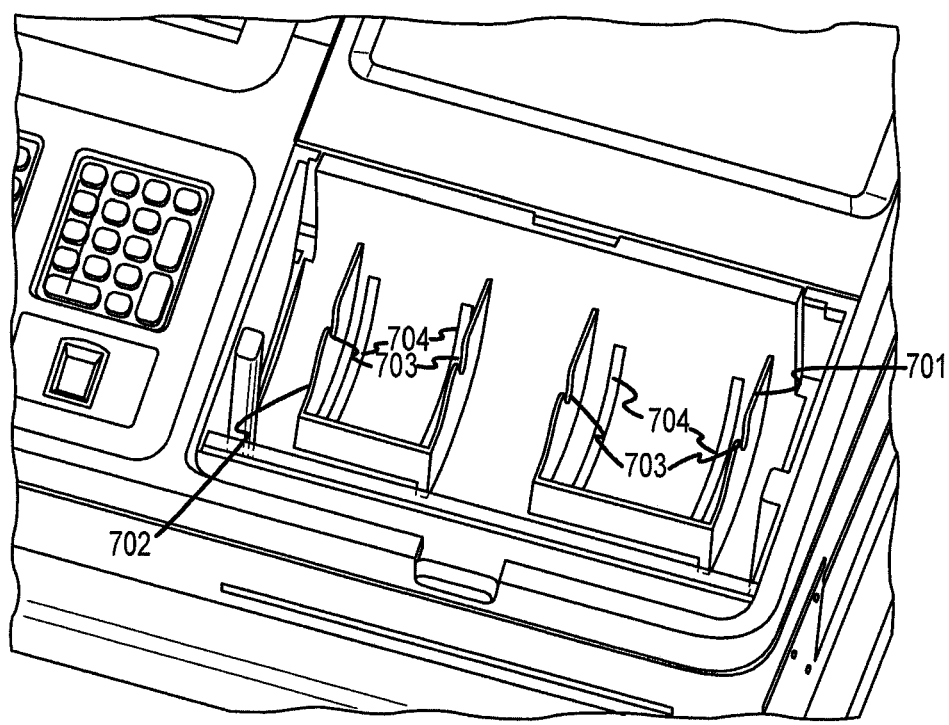
FIG. 7 illustrates a reverse angle view of the interior shown in FIG. 5.

FIG. 7 illustrates a reverse angle view of the interior of medication dispensing cabinet 400, showing the configuration of a receipt paper holder 701 and a label stock holder 702. As is visible in FIG. 7, paper holder 701 and label stock holder 702 may include features 703 for engaging spindles of rolls of media, should spindles be present. However, it is contemplated that either or both printers can use roll media that does not include a spindle. To facilitate the use of spindle-less media rolls, raised features 704 may be provided to support the media. Raised features 704 may be formed to be smooth, so as to allow the media to slide freely as it is dispensed.

Figure 8:
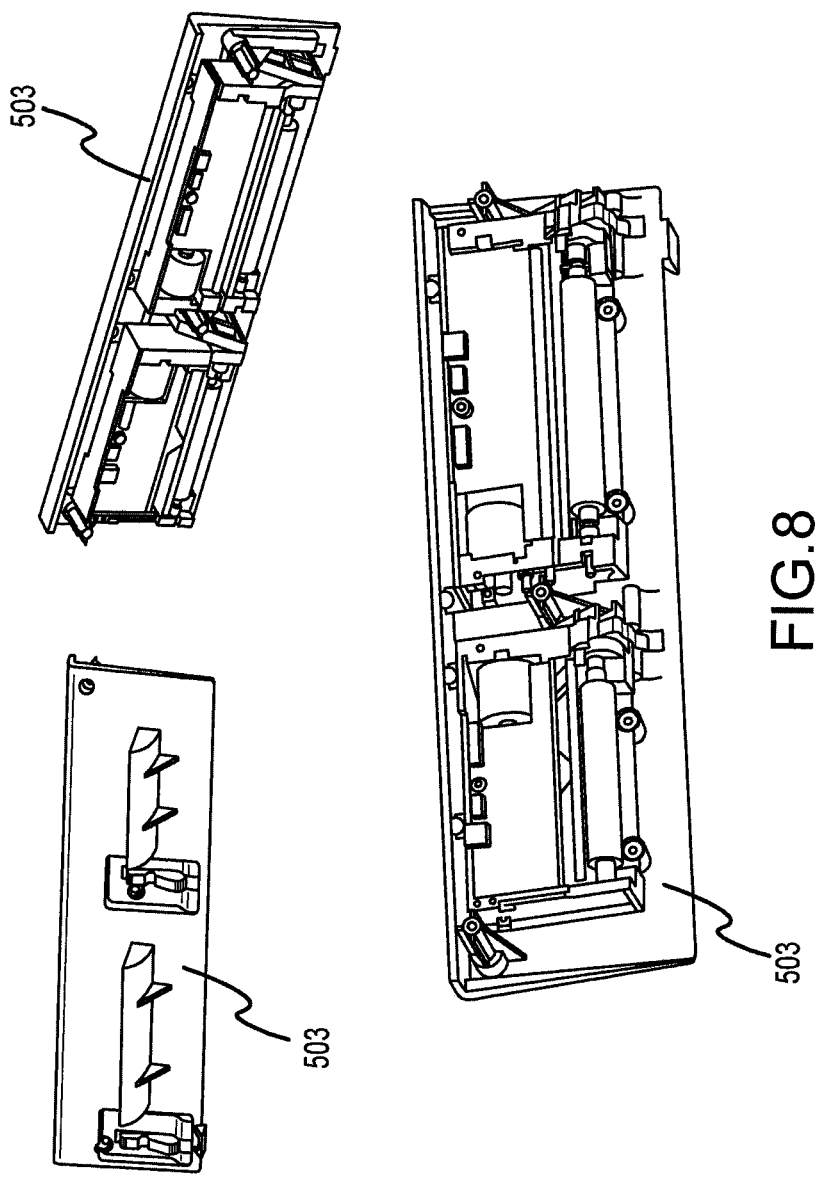
FIG. 8 illustrates additional details of the example medication dispensing cabinet of FIG. 4.

FIG. 8 illustrates additional details of the example medication dispensing cabinet 400. In this example embodiment, bezel 503 is mounted to the front lid assembly by three tabs and three screws. Printers 201 and 202 are mounted to bezel 503 using two screws each and ears. The ears in bezel 503 also help with routing necessary wires to printers 201 and 202. (The wires themselves are not shown in FIG. 8.)

Figure 9:
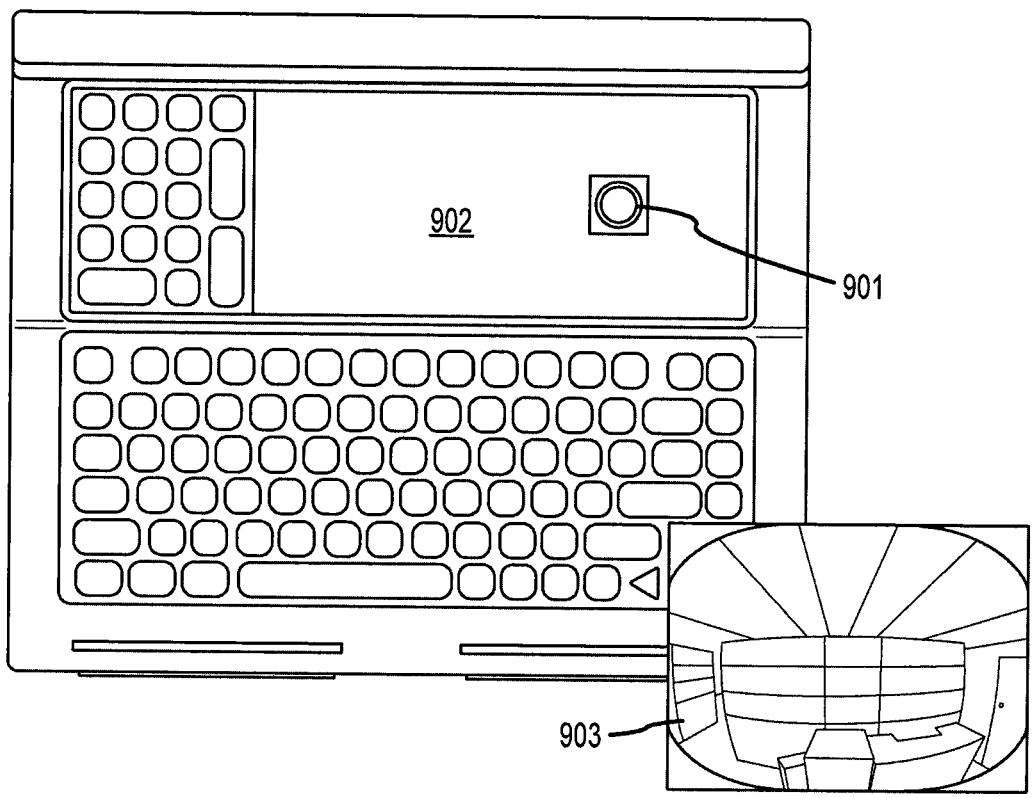
FIG. 9 illustrates the integration of a camera with a medication dispensing cabinet, according to embodiments.

According to another aspect, a medication dispensing cabinet such as cabinet 100 may include a camera. As is shown in FIG. 9, a camera 901 may be integrated into an area 902 near keyboard 104 of medication dispensing cabinet 100. Other locations are also possible. Camera 901 may provide a view such as view 903, encompassing an area where any user of cabinet 100 would be when accessing cabinet 100. Under control of controller 103, a photograph may be taken of each user who accesses cabinet 100, and the photograph stored for future reference. For example, the photograph may be associated with a usage log, for enhanced tracking of medications or supplies dispensed from cabinet 100. This capability may be especially helpful with the tracking of controlled substances, where only certain persons may be authorized to remove the substances from the cabinet. The stored photographs may also assist in detecting any attempted or actual illicit access to cabinet 100.

Figure 10A:
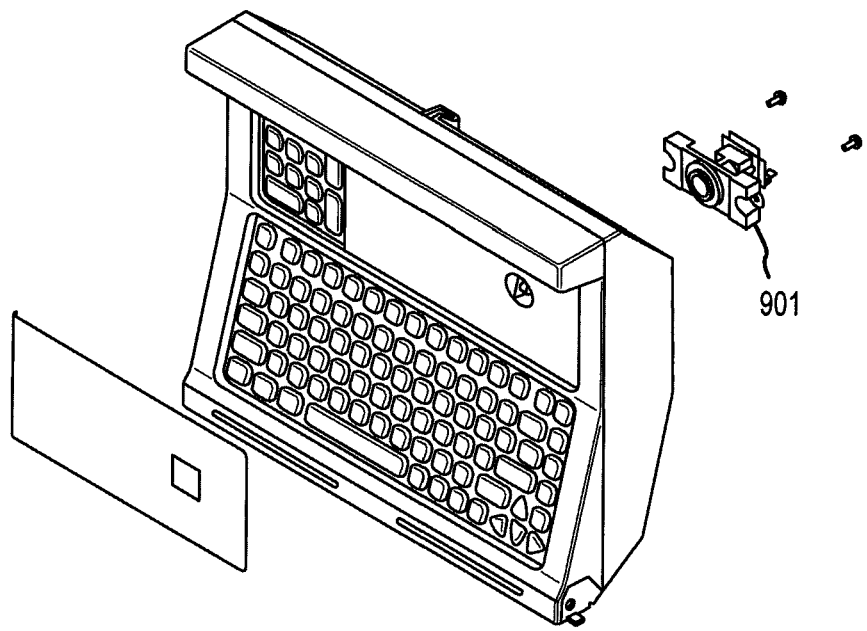
FIGS. 10A and 10B illustrate an example technique for integrating a camera into a medication dispensing cabinet.
Figure 10B:
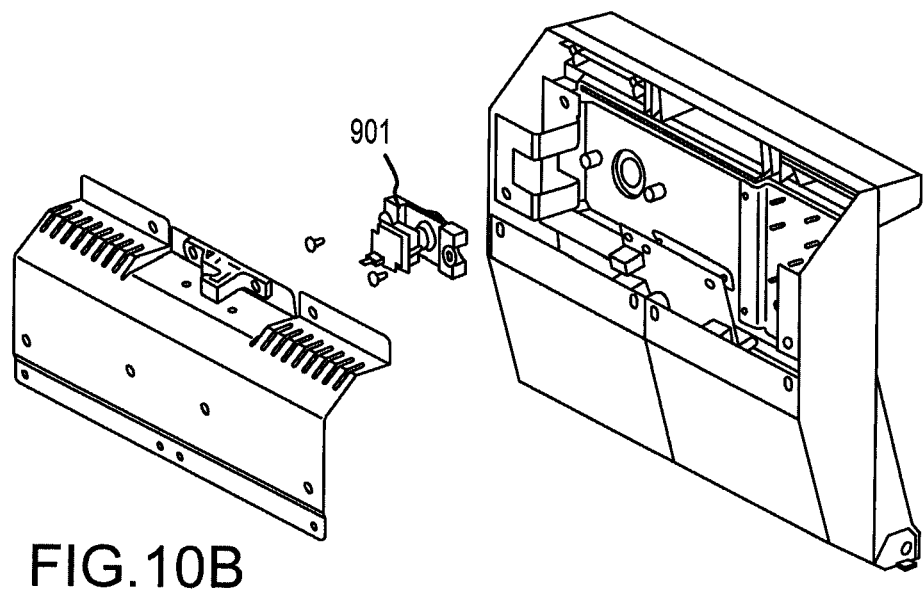

FIGS. 10A and 10B illustrate an example technique for integrating camera 901 into module 200 of example medication dispensing cabinet 100.

Figure 11:
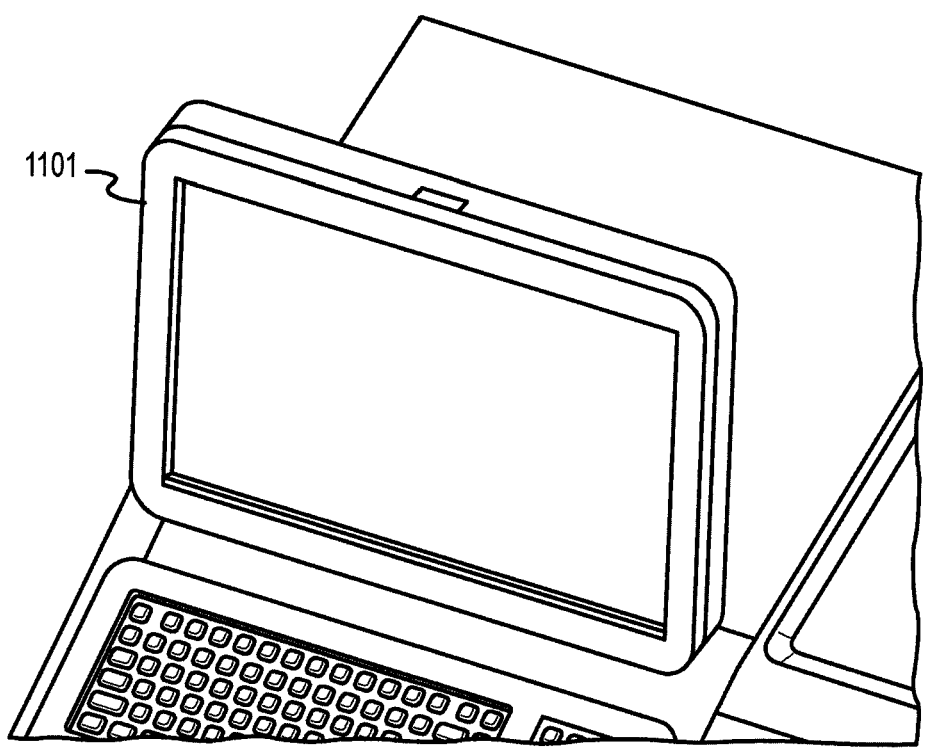
FIG. 11 shows a portion of the medication dispensing cabinet of FIG. 4, including a monitor.

A camera such as camera 901 may also be integrated into other kinds of cabinets, for example desktop medication dispensing cabinet 400. A portion of cabinet 400 is shown in FIG. 11. Cabinet 400 includes a free-standing monitor 1101, and a camera may conveniently be integrated into a bezel of monitor 1101, for example near the top center of the bezel. The camera may be optional, and when no camera is present, a standard bezel may be used. However, when a camera is present, a bezel having a viewing window may be used.

Figure 12:
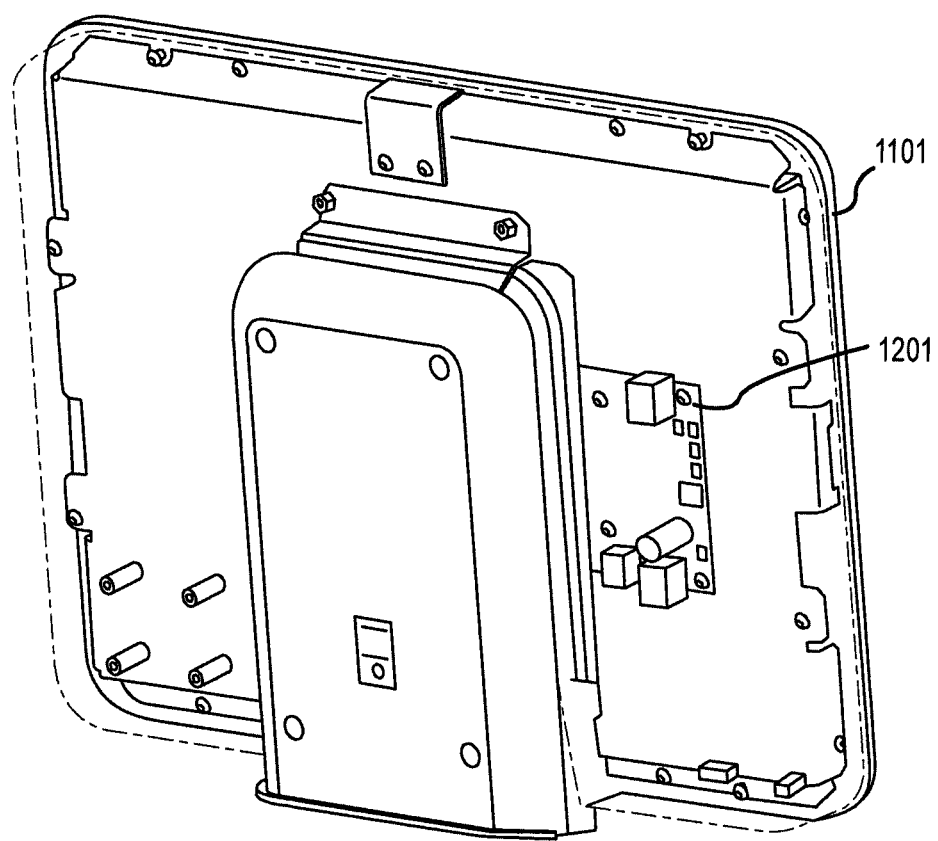
FIG. 12 shows the monitor of FIG. 11, from a reverse angle.

FIG. 12 illustrates monitor 1101 from a reverse angle. In some embodiments, the camera may be a module that includes a universal serial bus (USB) interface, and may be connected to a USB hub 1201 in monitor 1101.

Figure 13:
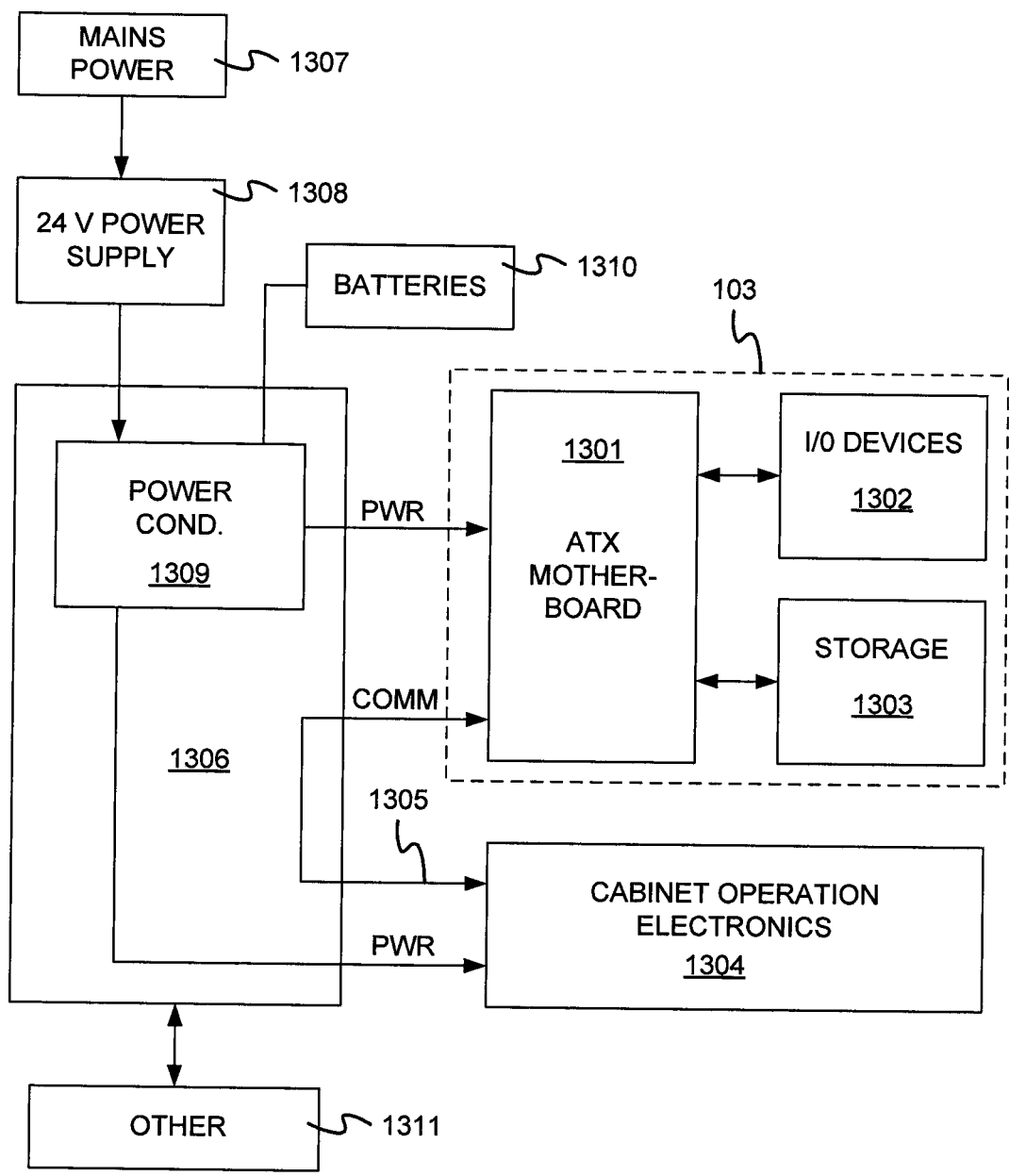
FIG. 13 illustrates an example electronic architecture of a medication dispensing cabinet.

In another aspect, FIG. 13 illustrates an example electronic architecture of a medication dispensing cabinet such as cabinet 100. As is explained above and illustrated in FIG. 13, controller 103 may include a computer system, including a processor, input/output interfaces, storage, and other components. In the example of FIG. 13, controller 103 includes a motherboard 1301 that conforms to the ATX (Advanced Technology Extended) configuration. For example, motherboard 1301 may include a microprocessor, expansion card slots, volatile memory, nonvolatile memory, and other computer system components. The volatile memory may include random access memory (RAM) for use as temporary program and data storage. The nonvolatile memory may include any combination of read only memory (ROM), flash memory, and other kinds of nonvolatile memory, and may hold such items as boot code for motherboard 1301, system settings, a basic input/output system (BIOS) and other items. In some embodiments, at least some of the contents of the nonvolatile memory may be remotely reprogrammable.

Controller 103 also includes input/output (I/O) devices 1302, which may include, for example, keyboard 104, keypad 105, and display 106. Other kinds of devices may be included. Controller 103 further comprises storage 1303, which may be, for example, long-term storage such as one or more hard disk or solid state drives. Storage 1303 may store an operating system for motherboard 1301, may store data such as an inventory of the cabinet, and may hold program instructions for control of the operation of the cabinet.

Cabinet electronics 1304 may include various actuators, indicators, and other components involved in controlling the cabinet, for example to lock and unlock drawers or doors under control of controller 103. Cabinet electronics 1304 may optionally also include one or more additional microprocessors or other logic circuitry. Motherboard 1301 communicates with cabinet electronics 1304 through communications link 1305.

Both controller 103 and cabinet electronics 1304 require electrical power for operation. A power distribution and communications circuit board 1306 conditions and distributes power to other system components, and also provides a communications pathway between controller 103 and cabinet electronics 1304. Power distribution and communications circuit board 1306 draws its power ultimately from the mains 1307. A first power supply 1308 may rectify the voltage obtained from mains 1307 and supply a single DC voltage to power distribution and communications circuit board 1306. Power conditioning circuitry 1309 on power distribution and communications circuit board 1306 extracts the various voltages needed to provide power rails to motherboard 1301 and other system components, and distributes the power.

Power distribution and communications circuit board 1306 may also interface with one or more batteries 1310, providing battery charging when mains power is available, and drawing power from batteries 1310 when necessary to power the system. Power distribution and communications circuit board 1306 may also provide an interface to other components 1311, which may include such components as a power-on indicator, a power switch, a diagnostic port connector, or other items or combinations of items.

Figure 14:
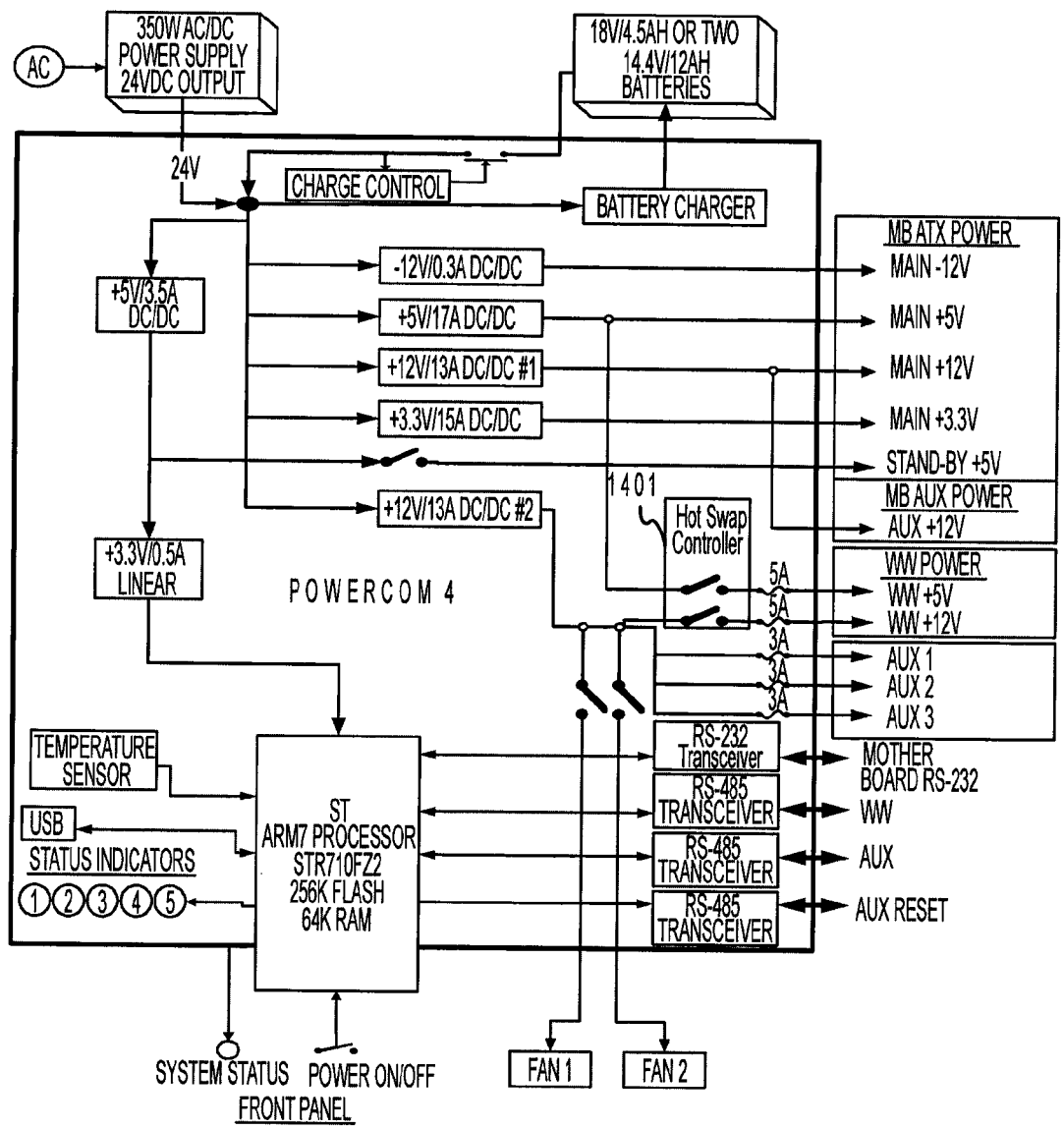
FIG. 14 schematically illustrates an example of a power distribution and communications circuit board.

FIG. 14 illustrates power distribution and communications circuit board 1306 in more detail, including showing the various voltage rails required by motherboard 1301, and examples of the kinds of communications signals that may be provided. In addition, power distribution and communications circuit board 1306 may include a hot swap controller 1401, enabling power to cabinet electronics 1304 to be interrupted so that drawers, button interfaces, or other components of the cabinet can be replaced without powering down controller 103.

In another aspect, a medication dispensing cabinet such as cabinet 100 may include security measures that control access to the cabinet. Access control may be especially useful when the cabinet stores legally controlled substances. In some embodiments, a user of the cabinet may be required to enter identifying information on keyboard 104 before being allowed access to the cabinet. The entered information is compared with a list of authorized users, and access is granted only if the entered information is found in the list. The authorization list may reside at controller 103, or may be on a remote server accessed over a network connection. Alternatively or additionally, a password or other security code may be required, and access may be granted only when the correct code is received.

Figure 15:
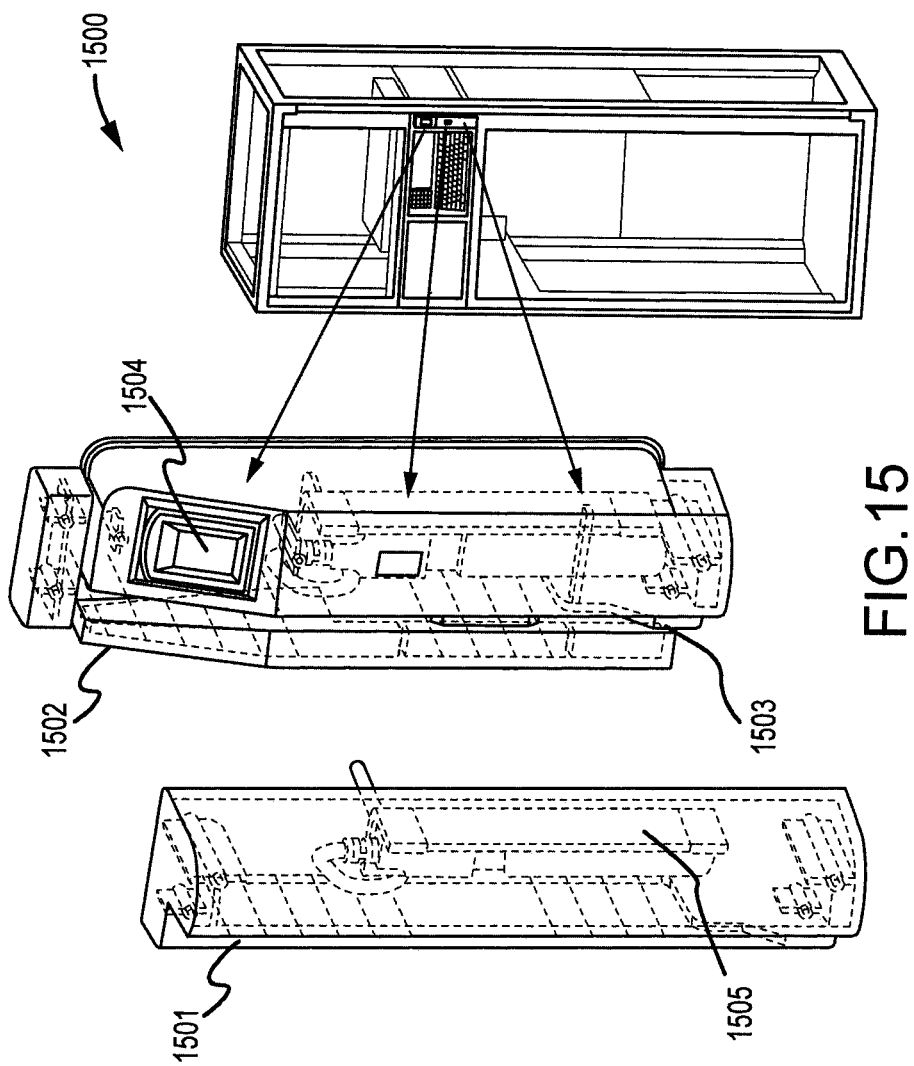
FIG. 15 illustrates a medication dispensing cabinet in accordance with embodiments, with optional reader devices.

In other embodiments, the cabinet may include one or more devices that can more quickly identify a person requesting access. FIG. 15 illustrates a medication dispensing cabinet 1500 in accordance with embodiments, with optional reader devices 1501 and 1502. Different kinds of readers may be provided, individually or in combinations.

In some embodiments, a reader may include a card swipe slot 1503. Each authorized user of cabinet 1500 may carry a card programmed with the user's identifying information. The user can swipe the card through the card swipe slot to provide the identifying information to cabinet 1500. The identifying information is compared, at cabinet 1500 or at a remote server, with a list of persons authorized to access cabinet 1500, and access is granted only if the information read at card swipe slot 1503 matches or is found on the list. The card carried by the user may be a magnetic stripe card, or a smart card may be used and cabinet 1500 may include a smart card reader. In other embodiments, cabinet 1500 may include a bar code scanner, and each user may carry a card, badge, or other item that is printed with a bar code identifying the user. In this scenario, the bar code is scanned to obtain the user's identifying information, which is then used similarly to grant or deny access to cabinet 1500.

Cabinet 1500 may also include a biometric sensor, such as fingerprint reader 1504. A user requesting access to cabinet 1500 may place a finger on fingerprint reader 1504, which reads the person's fingerprint. The fingerprint may then be checked to verify that it is on file as belonging to a person authorized to access cabinet 1500. If so, access is granted.

In some embodiments, cabinet 1500 may include a radio frequency identification (RFID) reader 1505. In RFID technology, a token is programmed with a unique code, and a reader wirelessly scans the code from the token. In passive RFID systems, wireless signals from the reader activate the token, enabling it to wirelessly return the code to the reader. In active RFID systems, the token may include a power source such as a battery, and may be able to provide the code from greater distance from the reader than in passive systems. A user requesting access to cabinet 1500 may carry a token, and the code from the token may be automatically scanned when the token comes into proximity with cabinet 1500. The code is compared with a list of codes for which access is authorized, and access is granted if a match is found.

Depending on the level of security required for the contents of cabinet 1500, multi-factor authentication may be required. For example, to be granted access to cabinet 1500, a user may be required to provide a token having an approved code (something the user has), and may also be required to provide a correct password (something the user knows). The user may also be required to provide a fingerprint (something the user is). Various identification factors may be used, in any combination.

According to another aspect, controller 103 may store data redundantly for additional reliability and data integrity. For example, motherboard 1301 may include a RAID (redundant array of independent disks) controller, and storage 1303 may include multiple storage devices. The storage devices may utilize rotating media such as hard disks, or may utilize solid state memory such as flash memory. (While RAID technology is often utilized with spinning disks, the concept is not so limited, and redundant solid state memories may be considered a RAID system.) Redundant storage of cabinet inventory and patient information reduces the risk of data loss from storage device failure, and thus also reduces the risk that inventory records or patient information will be lost.

Figure 16:
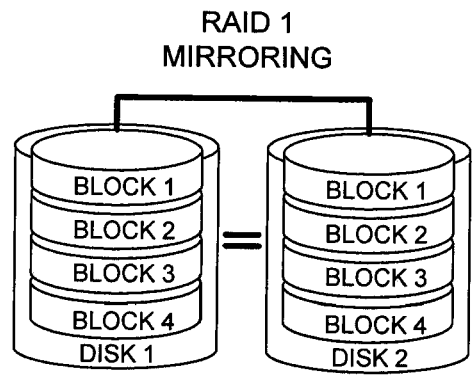
FIG. 16 illustrates one implementation of RAID technology.

Different levels of RAID protection are available. In "RAID level 1", illustrated in FIG. 16, all data is mirrored to a redundant storage device. More complex RAID levels may also distribute data over multiple storage devices to enhance data read speed and to enable error correction. The failure rate of storage devices can be a significant contributor to a medical embedded system's expected rate of failure, whether due to moving parts and shock intolerance (for spinning disks) or excessive flash write cycle fatigue (for solid state drives). Reliability is enhanced because it is extremely unlikely that two or more disk drives in a single system will fail at the same time, so redundancy keeps the system running long enough to replace malfunctioning disks when no patient's care is at stake.

Data integrity is also enhanced. Some data processed on medication distribution machines include the dosage, quantity and timing of life-critical medications. Safeguards including immediate detection and alerting of data errors at every level of the system design is important for patient safety. RAID provides another overlapping safety measure for patient and medication data.

Figure 17:
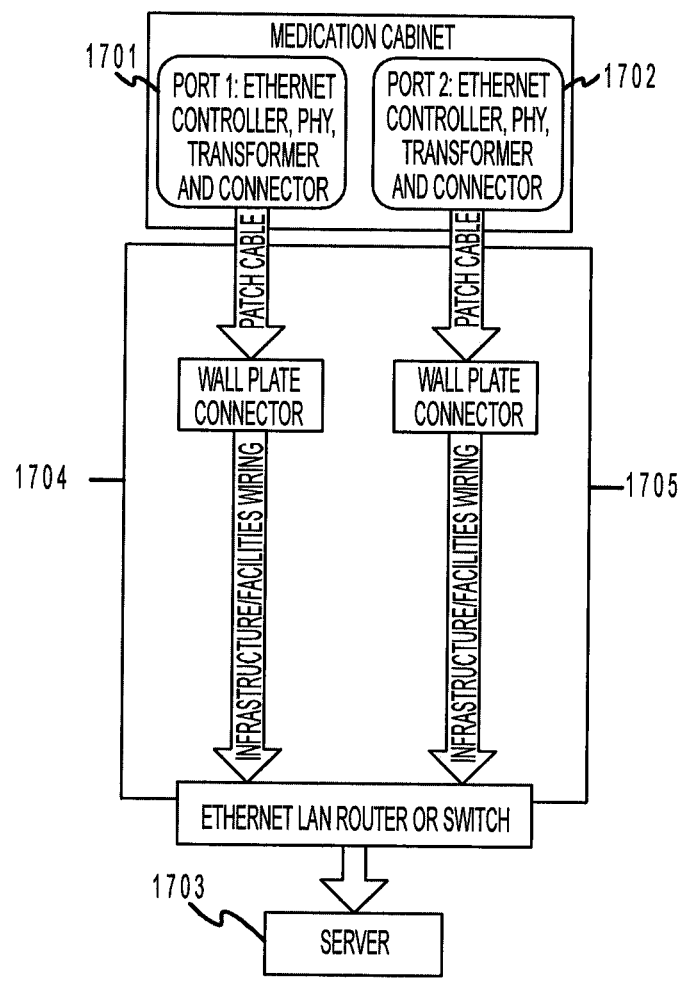
FIG. 17 illustrates a medication dispensing cabinet according to embodiments, having redundant network connections.

In another aspect, a medication dispensing cabinet according to embodiments may include redundant network connections, for additional reliability. This arrangement is illustrated in FIG. 17. Ports 1701 and 1702 may be provided on motherboard 1301. The medication cabinet may communicate through the local facility computer network with a server 1703 that pushes and pulls medication orders, patient information, accounting of completed transactions and other safety critical information. Redundancy of the network link for failover protection is provided by the use of duplicate network paths 1704 and 1705. Automatic switch-over of LAN communications to the second network link happens when failures occur anywhere in the path including the Ethernet controller or transformer on the cabinet motherboard, ethernet patch cable from machine to wall connector, or facility wiring through hospital walls to the main hospital router or switch. The use of failover pairs may already exist for LANs on the other side of the switch or router within a typical IT system. This helps guarantee that each cabinet in the hospital has the latest and most accurate information needed to assist with a patient, who may be moved from one area to another. Alternately, the dual network interface can be configured to improve network throughput by using both paths in parallel or to create isolated networks for LAN and WAN for secure and less secure functions.

Figure 18:
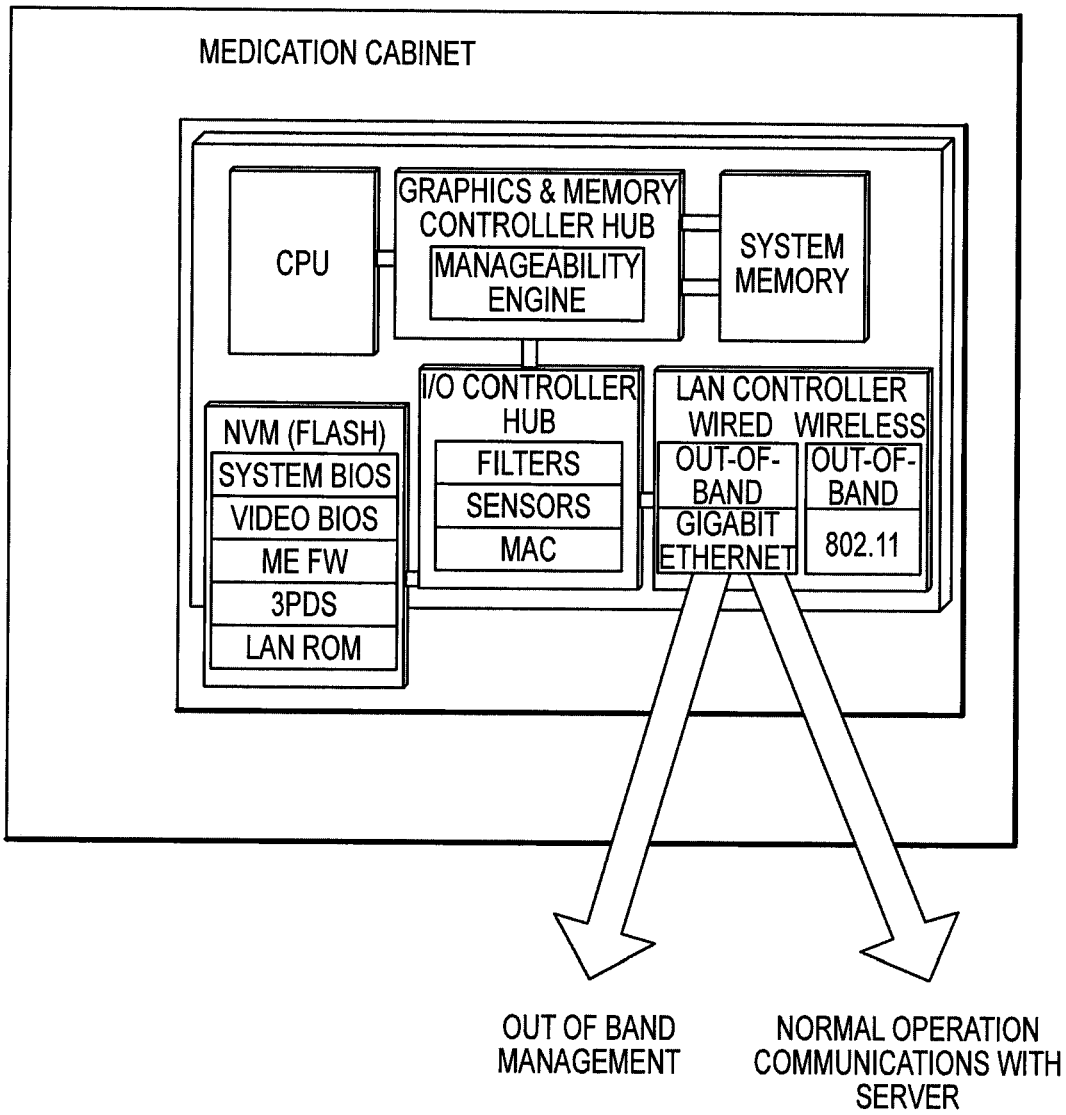
FIG. 18 illustrates a medication dispensing cabinet according to embodiments, having a remote administration capability.

According to another aspect, a controller in a medication dispensing cabinet according to embodiments may include a remote administration capability. This capability is illustrated in FIG. 18. For example, controller 103 may include hardware-based, remote management through an encrypted, out-of-band network communication channel independent of the state of the computer's operating system, power state, and health of hardware components such as disks and memory. This feature allows a facility's information technology department to better discover, heal, and protect their medication cabinets. For example, such a capability may be implemented using Advanced Management Technology (AMT) available on some computer systems using microprocessors manufactured by Intel Corporation of Santa Clara, Calif., USA.

The out of band channel may be used for various functions. For example, controller 103 may be remotely managed by combining the out of band channel with scripting to automate maintenance and service, or to check inventory of hardware. The system may also enhance security. For example, when the medication cabinet is powered and its computer booted, the out of band channel can be used to securely monitor for unauthorized software agents, or to redirect the console to a different remote computer. Network traffic may be filtered, for example by port-blocking, rate-limiting, or fully isolating a cabinet that might be compromised or infected. The system may also be used for power management. For example, the power state of the medication cabinet may be changed remotely, such as for turning it on and off. This can be used to power cycle a machine if it becomes unstable or frozen, improving the operational time in a medical environment. The system may also be used for remote configuration of controller 103, for example reprogramming of the BIOS or remotely re-imaging of storage drives.

While the embodiments described above illustrate the dispensing of prescribed medications, it will be recognized that dispensing cabinets in accordance with embodiments may be used for dispensing medications that do not require doctors prescriptions, or supplies such as bandages, gloves, or other items. Cabinets according to embodiments may also be used in an anesthesia setting.

Systems according to embodiments may also include features for promoting and facilitating proper labeling of medications or other supplies removed from a dispensing cabinet. For example, accepted patient care standards require that any medications, medication containers, and solutions must be labeled unless they are to be administered immediately. Failure to label or improper labeling may result in medication errors, missed doses, unplanned work for medical staff, and waste of medication.

An integrated label printer such as printer 202 provides a mechanism for printing labels in conjunction with dispensing. In addition, a dispensing cabinet according to embodiments may be programmed to direct a health care worker through a workflow that facilitates convenient and accurate labeling.

In one example configuration, the dispensing cabinet is configured to automatically print a label each time an item is issued from the cabinet. FIG. 19A illustrates a configuration menu for configuring the system for various behaviors, including automatic printing. Menu 1900 may be displayed, for example, by the controller of the dispensing cabinet, and a nurse or other user may select and de-select menu items in order to configure the system. Once a label is printed, the user can then attach the newly-printed label to the container into which the item is placed, for example onto a syringe into which an injectable medication is placed. In some cases, the label may be placed directly on the medication or other dispensed item.

FIG. 19B illustrates a workflow for automatic label printing. In step 1901, a nurse or other health care worker accesses the dispensing cabinet and selects a patient for whom a medication is to be dispensed. In step 1902, the nurse indicates that a particular medication is to be dispensed. For example, the nurse may click or touch a "Remove Now" button in a user interface displayed on a monitor such as monitor 1101. In step 1903, the system prompts the nurse to remove the item from the correct bin. For example, a message such as "Open lid of flashing bin for this medication" may be displayed. In step 1904, the label prints automatically. In step 1905, the nurse is prompted to place the label on the medication. For example, a message such as "Apply the label to the correct medication" may be displayed.

FIG. 19C illustrates an example printed label. Information on the label may include data about the item, the patient, special instructions, or the user who printed the label. This data may come from external systems.

Within this general workflow, other options may be provided. For example, the system may be configured to include a barcode on the printed label, identifying the medication, to facilitate later bedside documentation of use of the dispensed medication. Including a barcode on the printed label eliminates the need to have the original medication container present at the time the medication is administered to the patient. In some embodiments, especially when a high-risk medication is being dispensed, a confirmation step may be required. For example, the system may require that a barcode be scanned from the original medication package as it is removed from the cabinet, so that the identity of the dispensed medication can be verified. The system may be configured such that no label is printed when confirmation is required but not received. The health care worker may be able to override the bar code scan, for example to accommodate situations where the barcode on the original medication package is not readable. The health care worker may be required to enter an explanation of justification for overriding the barcode scan requirement.

FIG. 20A illustrates configuration menu 1900 with the bar code and confirmation options selected. FIG. 20B illustrates a workflow according to this embodiment. Several of the steps are identical to those of FIG. 19B. In an additional step 2001, a confirmation is required. At step 2002, the system determines whether the confirmation has been received, for example whether a successful barcode scan from the original medication package is received. If so, the label is printed for attachment to the dispensed medication. If no confirmation is received, for example the nurse has overridden the requirement for confirmation, no label is printed, as indicated at 2003.

In a second example workflow, labels may not be printed automatically, but may be printed on demand, in conjunction with the dispensing of items. As in the workflows for automatic printing, confirmation may be required, and barcodes may optionally included or excluded from the printed labels, depending on the current configuration of the dispensing cabinet.

In a third example workflow, labels may be printed for medications or other items have been previously dispensed or issued from the dispensing cabinet. For example, a user may print a label for an item that was dispensed earlier in the day. In this workflow, the nurse uses the controller of the dispensing cabinet to access a record of medication or other item dispensed for a particular patient, and indicates that a label is to be printed for the item. As in the other workflows, confirmation may be required, and a barcodes may be optionally included or excluded from the printed label, depending on the current configuration of the dispensing cabinet. A user of the dispensing cabinet may be able to print a label for an item that was dispensed by a different user.

Whichever workflow is enabled, the nurse may preferably be able to complete the issue of the medication whether a label is successfully printed or not. In some embodiments, the nurse or other health care worker may be able to re-print a label, if necessary, for example if a label is damaged in retrieving it from the label printer. In some embodiments, the system may be configured to calculate beyond-use dates for dispensed medications, and to print the beyond-use date on the printed labels.

In a particular dispensing session, multiple items may be dispensed according to a single medication order. Preferably, a separate label prints for each dispensed item. In some orders, not all items may be configured for automatic label printing. In some embodiments, whenever at least one item in a medication order is configured for automatic label printing, labels are automatically printed for all of the items in the order.

The system may be configurable to select different workflows and options. For example, the system may be configurable to require confirmation or to not require confirmation. In another example, the system may be configurable to include a barcode on the printed label, or to exclude the barcode. In yet another example, the system may be configurable to include a calculated beyond use date on a printed label, or to exclude the beyond use date. FIG. 19A shows one technique for configuring the system, but other methods may be envisioned.

Preferably, the label printer can report to the dispensing cabinet controller when attention is required at the printer. For example, the printer may include sensors to detect when the label stock needs to be replenished, when the printer has not been properly configured for printing, and the like. The health care worker may be notified with real time messages, for example messages displayed on monitor 1101, indicating that attention is needed to the printer. Multiple cabinets can report status and transactions back to a central server. The server may consolidate and aggregate data into reports used by administrators to review stats of label printers and printing statistics.

It will be understood that any workable combination of any features described herein is also considered to be disclosed.

The invention has now been described in detail for the purposes of clarity and understanding. However, those skilled in the art will appreciate that certain changes and modifications may be practiced within the scope of the appended claims.

What is claimed is:

1. A medication dispensing cabinet, comprising:
   at least one lockable storage compartment;
   a controller that controls access to the interior of the at least one lockable storage compartment by a user to whom an item is to be dispensed; and
   two printers coupled to the controller and integrated into the medication dispensing cabinet, wherein the two printers comprise a receipt printer and a label printer, and wherein the two printers use different media;
   and wherein the both of the two printers provide their output outside the medication dispensing cabinet;
   and wherein the medication dispensing cabinet defines a single common opening through which to deliver items from the label printer and the receipt printer.

2. The medication dispensing cabinet of claim 1, wherein the two printers mount to a common bezel.

3. The medication dispensing cabinet of claim 1, wherein at least one of the printers comprises a printing stock holder for holding a roll of printing stock, and wherein the printing stock holder includes a curved surface shaped to approximately conform to the outside of the roll of printing stock, the curved surface including a raised feature formed to be smooth, so as to allow the stock to slide freely as it is dispensed.

4. The medication dispensing cabinet of claim 2, further comprising paper guides for the receipt printer and the label printer molded into a rear surface of the common bezel.

* * * * *